US010123605B2

(12) United States Patent
Luu

(10) Patent No.: US 10,123,605 B2
(45) Date of Patent: Nov. 13, 2018

(54) HAIR CUTTING DEVICE

(71) Applicant: Linda Luu, Los Angeles, CA (US)

(72) Inventor: Linda Luu, Los Angeles, CA (US)

(*) Notice: Subject to any disclaimer, the term of this patent is extended or adjusted under 35 U.S.C. 154(b) by 406 days.

(21) Appl. No.: 14/566,626

(22) Filed: Dec. 10, 2014

(65) Prior Publication Data
US 2016/0166039 A1 Jun. 16, 2016

(51) Int. Cl.
B26B 17/00 (2006.01)
A45D 26/00 (2006.01)
A61C 3/10 (2006.01)

(52) U.S. Cl.
CPC .......... A45D 26/0066 (2013.01); B26B 17/00 (2013.01); A61C 3/10 (2013.01)

(58) Field of Classification Search
CPC ........ A45D 26/0066; B26B 17/00; A61C 3/10
USPC .......... 30/175–179, 234–236, 131, 134, 143; 294/99.1–99.2; 606/131–133, 211, 174, 606/167
See application file for complete search history.

(56) References Cited

U.S. PATENT DOCUMENTS

| 1,610,925 | A |   | 12/1926 | Bryan |   |
|---|---|---|---|---|---|
| 2,608,698 | A | * | 9/1952 | Mindheim | D03J 1/00 294/99.2 |
| 2,865,099 | A | * | 12/1958 | Blackwood | A61B 17/0467 30/134 |
| 3,659,343 | A | * | 5/1972 | Straus | A61B 17/0467 30/124 |
| 4,020,846 | A |   | 5/1977 | Stokes |   |
| 4,034,473 | A | * | 7/1977 | May | A61B 17/0467 30/181 |
| 4,053,979 | A | * | 10/1977 | Tuthill | A61B 17/0467 30/124 |
| 4,452,106 | A |   | 6/1984 | Tartaglia |   |
| 4,541,428 | A |   | 9/1985 | Scherrer |   |
| 4,693,246 | A | * | 9/1987 | Reimels | A61B 17/30 606/148 |
| 5,015,252 | A |   | 5/1991 | Jones |   |
| 5,016,353 | A | * | 5/1991 | Iten | A61B 17/0467 30/124 |
| 5,047,037 | A | * | 9/1991 | Brandfield | A61B 17/0467 30/124 |
| 5,060,329 | A |   | 10/1991 | Hudson |   |
| 5,226,237 | A | * | 7/1993 | Rancour | B26B 9/02 30/187 |
| D714,998 | S |   | 10/2014 | Luu |   |

(Continued)

Primary Examiner — Ghassem Alie
Assistant Examiner — Nhat Chieu Do
(74) Attorney, Agent, or Firm — Roeder & Broder LLP; James P. Broder

(57) ABSTRACT

A hair cutting device (10) comprises a first arm (12) having (i) a first arm proximal end (20), (ii) a first arm distal end (22), (iii) a first arm connected section (24), (iv) a first arm diverging section (26), (v) a first arm converging section (28), (vi) a cutting surface (52), and (vii) a first arm width (12W); and an opposed second arm (14) having (i) a second arm proximal end (38), (ii) a second arm distal end (40), (iii) a second arm connected section (42), (iv) a second arm diverging section (44), (v) a second arm converging section (46), (vi) a cutting blade (54), and (vii) a second arm width (14W). The second arm width (14W) is narrower than the first arm width (12W) through a substantial entirety of the second arm converging section (46) and the first arm converging section (28).

16 Claims, 4 Drawing Sheets

(56) References Cited

U.S. PATENT DOCUMENTS

2006/0260135 A1* 11/2006 Khan-Sullman ... A61B 17/0467
30/134
2007/0251100 A1 11/2007 Fisk \* cited by examiner

HAIR CUTTING DEVICE

BACKGROUND

Many people desire to precisely trim the hairs that exist in certain delicate and/or hard-to-access places on the body. For example, many people desire to precisely trim eyelashes and/or eyebrow hairs. Accordingly, it is desired to have a precise hair cutting device that can safely and precisely position and trim the eyelashes and/or eyebrow hairs.

SUMMARY

The present invention is directed toward a hair cutting device comprising a first arm and an opposed second arm. In certain embodiments, the first arm has (i) a first arm proximal end, (ii) a first arm distal end, (iii) a first arm connected section that extends away from the first arm proximal end, (iv) a first arm diverging section that extends away from the first arm connected section, (v) a first arm converging section that extends away from the first arm diverging section to the first arm distal end, (vi) a cutting surface formed along a first arm inner surface of the first arm substantially adjacent to the first arm distal end, and (vii) a first arm width. Additionally, in such embodiments, the second arm has (i) a second arm proximal end, (ii) a second arm distal end, (iii) a second arm connected section that extends away from the second arm proximal end, the second arm connected section being secured to the first arm connected section, (iv) a second arm diverging section that extends away from the second arm connected section, the second arm diverging section gradually getting farther away from the first arm diverging section, (v) a second arm converging section that extends away from the second arm diverging section to the second arm distal end, the second arm converging section gradually getting closer to the first arm converging section, (vi) a cutting blade along a second arm inner surface of the second arm substantially adjacent to the second arm distal end, and (vii) a second arm width. Further, in such embodiments, the second arm width is narrower than the first arm width through a substantial entirety of the second arm converging section and the first arm converging section.

In one embodiment, the first arm distal end includes a substantially flat, blunted first arm tip, and the second arm distal end includes a sharp, pointed second arm tip.

Additionally, in some embodiments, the first arm connected section has a connected length of between a range of greater than approximately ten percent and less than approximately twenty percent of an overall device length; the first arm diverging section has a diverging length of between a range of greater than approximately seventy percent and less than approximately eighty percent of the overall device length; and the first arm converging section has a converging length of between a range of greater than approximately five percent and less than approximately fifteen percent of the overall device length. In one such embodiment, the second arm connected section has a connected length that is substantially equal to the connected length of the first arm connected section; the second arm diverging section has a diverging length that is substantially equal to the diverging length of the first arm diverging section; and the second arm converging section has a converging length that is substantially equal to the converging length of the first arm converging section.

Further, in certain embodiments, the first arm diverging section and the second arm diverging section diverge from one another at a diverging angle of between a range of greater than approximately two degrees and less than approximately ten degrees when the cutting device is in an open position. Additionally, in one such embodiment, the first arm converging section and the second arm converging section converge toward one another at a converging angle of between a range of greater than approximately ten degrees and less than approximately twenty-five degrees when the cutting device is in the open position.

In one embodiment, the cutting blade includes a first angled side and a second angled side that converge toward one another to provide a sharp, cutting edge that is configured to selectively engage the cutting surface during a cutting operation, and a convex curved outer surface that is on the opposite side from the cutting edge. Additionally, the cutting blade can be integrally formed with the second arm.

Moreover, in one embodiment, the cutting blade includes a cutting edge that is configured to gradually engage the cutting surface during a cutting operation from a blade tip at a distal end of the cutting blade to a proximal end of the cutting blade.

In another application, the present invention is directed toward a hair cutting device comprising (A) a first arm having (i) a first arm proximal end, (ii) a first arm distal end, (iii) a first arm connected section that extends away from the first arm proximal end, (iv) a first arm diverging section that extends away from the first arm connected section, (v) a first arm converging section that extends away from the first arm diverging section to the first arm distal end, and (vi) a cutting surface formed along a first arm inner surface of the first arm substantially adjacent to the first arm distal end; and (B) an opposed second arm having (i) a second arm proximal end, (ii) a second arm distal end, (iii) a second arm connected section that extends away from the second arm proximal end, the second arm connected section being secured to the first arm connected section, (iv) a second arm diverging section that extends away from the second arm connected section, the second arm diverging section gradually getting farther away from the first arm diverging section, (v) a second arm converging section that extends away from the second arm diverging section to the second arm distal end, the second arm converging section gradually getting closer to the first arm converging section, and (vi) a cutting blade along a second arm inner surface of the second arm substantially adjacent to the second arm distal end, the cutting blade being configured to selectively engage the cutting surface during a cutting operation, the cutting blade including a first angled side and a second angled side that converge toward one another to provide a sharp, cutting edge, and a convex curved outer surface that is on the opposite side from the cutting edge.

In yet another application, the present invention is further directed toward a hair cutting device comprising (A) a first arm having (i) a first arm proximal end, (ii) a first arm distal end including a substantially flat, blunted first arm tip, (iii) a first arm connected section that extends away from the first arm proximal end, (iv) a first arm diverging section that extends away from the first arm connected section, (v) a first arm converging section that extends away from the first arm diverging section to the first arm distal end, (vi) a cutting surface formed along a first arm inner surface of the first arm substantially adjacent to the first arm distal end, and (vii) a first arm width; and (B) an opposed second arm having (i) a second arm proximal end, (ii) a second arm distal end including a sharp, pointed second arm tip, (iii) a second arm connected section that extends away from the second arm proximal end, the second arm connected section being secured to the first arm connected section, (iv) a second arm diverging section that extends away from the second arm connected section, the second arm diverging section gradually getting farther away from the first arm diverging section, (v) a second arm converging section that extends away from the second arm diverging section to the second arm distal end, the second arm converging section gradually getting closer to the first arm converging section, (vi) a cutting blade along a second arm inner surface of the second arm substantially adjacent to the second arm distal end, the cutting blade being configured to selectively engage the cutting surface during a cutting operation, the cutting blade including a first angled side and a second angled side that converge toward one another to provide a sharp, cutting edge, and a convex curved outer surface that is on the opposite side from the cutting edge; wherein the second arm width is narrower than the first arm width through a substantial entirety of the second arm converging section and the first arm converging section.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION

Figure 1:
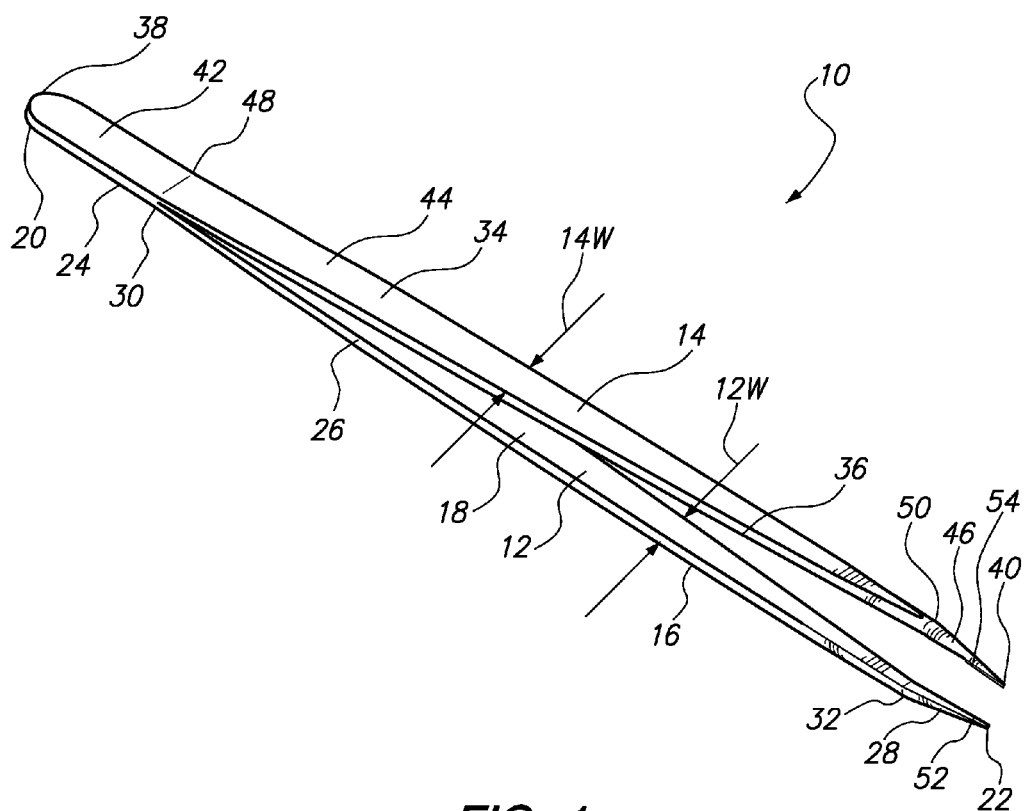
FIG. 1 is a perspective view of an embodiment of a hair cutting device having features of the present invention.

FIG. 1 is a perspective view of an embodiment of a hair cutting device 10 (hereinafter sometimes referred to as a "cutting device" or simply as a "device") having features of the present invention. The design of the cutting device 10 can be varied as desired. As shown in the embodiment illustrated in FIG. 1, the cutting device 10 includes a first arm 12 and an opposed second arm 14 that are of substantially similar length, and that are fixedly secured together.

It should be appreciated that the use of the terms "first arm" and "second arm" is merely for convenience and ease of description, and either arm 12, 14 can be referred to as the "first arm" and/or the "second arm".

In this embodiment, the first arm 12 includes a first arm outer surface 16 (illustrated more clearly in FIG. 5), a first arm inner surface 18, a first arm proximal end 20 and a first arm distal end 22. Additionally, as described in greater detail herein below, the first arm 12 has a first arm width 12W that varies over the length of the first arm 12. For example, as shown in FIG. 1, the first arm width 12W and/or the first arm 12 tapers generally inwardly, i.e. generally narrows while moving in a direction from the first arm proximal end 20 to the first arm distal end 22.

Further, the first arm 12 can also be described as including a first arm connected section 24, a first arm diverging section 26 and a first arm converging section 28 that cooperate to extend the length of the first arm 12 from the first arm proximal end 20 to the first arm distal end 22. Moreover, the first arm 12 also includes a first arm flex point 30 that defines the junction and/or transition between the first arm connected section 24 and the first arm diverging section 26; and a first arm angle adjustment point 32 that defines the junction and/or transition between the first arm diverging section 26 and the first arm converging section 28. In one embodiment, the first arm flex point 30 and the first arm angle adjustment point 32 can provide a substantially discrete, sharp transition point between adjacent sections of the first arm 12. Alternatively, the first arm flex point 30 and/or the first arm angle adjustment point 32 can provide a somewhat gradual or rounded profile for the transition between adjacent sections of the first arm 12.

Somewhat similarly, the second arm 14 includes a second arm outer surface 34, a second arm inner surface 36 (illustrated more clearly in FIG. 5), a second arm proximal end 38 and a second arm distal end 40. Additionally, as described in greater detail herein below, the second arm 14 has a second arm width 14W that varies over the length of the second arm 14. For example, as shown in FIG. 1, the second arm width 14W and/or the second arm 14 tapers generally inwardly, i.e. generally narrows while moving in a direction from the second arm proximal end 38 to the second arm distal end 40.

Further, the second arm 14 can also be described as including a second arm connected section 42, a second arm diverging section 44, and a second arm converging section 46 that cooperate to extend the length of the second arm 14 from the second arm proximal end 38 to the second arm distal end 40. Moreover, the second arm 14 also includes a second arm flex point 48 that defines the junction and/or transition between the second arm connected section 42 and the second arm diverging section 44; and a second arm angle adjustment point 50 that defines the junction and/or transition between the second arm diverging section 44 and the second arm converging section 46. In one embodiment, the second arm flex point 48 and the second arm angle adjustment point 50 can provide a substantially discrete, sharp transition point between adjacent sections of the second arm 14. Alternatively, the second arm flex point 48 and/or the second arm angle adjustment point 50 can provide a somewhat gradual or rounded profile for the transition between adjacent sections of the second arm 14.

As noted above, the first arm 12 is fixedly secured to the second arm 14. More particularly, the first arm 12 includes the first arm connected section 24 that extends away from and/or is substantially adjacent to the first arm proximal end 20, and the second arm 14 includes the second arm connected section 42 that extends away from and/or is substantially adjacent to the second arm proximal end 38. As shown in FIG. 1, the first arm connected section 24 is fixedly secured to the second arm connected section 42. The first arm 12 can be secured to the second arm 14 in any suitable manner. For example, in one non-exclusive alternative embodiment, the first arm connected section 24 is fused to the second arm connected section 42. Alternatively, the first arm 12 can be secured to the second arm 14 in a different manner, e.g., with welds, screws, bolts, adhesives, or any other suitable manner.

Additionally, the first arm 12 further includes the first arm diverging section 26 that extends from and/or is substantially adjacent to the first arm connected section 24, and the second arm 14 further includes the second arm diverging section 44 that extends from and/or is substantially adjacent to the second arm connected section 42. As shown, and as more clearly illustrated in FIG. 5, within the diverging sections 26, 44, the first arm 12 and the second arm 14 gradually get farther apart as the diverging sections 26, 42 move from the connected sections 24, 42 to the converging sections 28, 46. Stated in another manner, the arms 12, 14 gradually diverge from one another as the arms 12, 14 extend from the flex points 30, 48 to the angle adjustment points 32, 50, respectively.

Further, as shown, the first arm 12 also includes the first arm converging section 28 that extends from the first arm diverging section 26 to the first arm distal end 22, and the second arm 14 also includes the second arm converging section 46 that extends from the second arm diverging section 44 to the second arm distal end 40. Moreover, as noted above, the first arm 12 includes the first arm angle adjustment point 32 that functions as the transition between the first arm diverging section 26 and the first arm converging section 28; and the second arm 14 includes the second arm angle adjustment point 50 that functions as the transition between the second arm diverging section 44 and the second arm converging section 46. As shown, and as more clearly illustrated in FIG. 5, within the converging sections 28, 46, the first arm 12 and the second arm 14 gradually get closer together as the converging sections 28, 44 move from the diverging sections 26, 44 to the distal ends 22, 40. Stated in another manner, the arms 12, 14 gradually converge toward one another as the arms 12, 14 extend from the angle adjustment points 32, 50 to the distal ends 22, 40, respectively.

Still further, the first arm 12 includes a cutting surface 52 along the first arm inner surface 18 near and/or substantially adjacent to the first arm distal end 22; and the second arm 14 includes a cutting blade 54 positioned along the second arm inner surface 36 near and/or substantially adjacent to the second arm distal end 40. In some embodiments, the cutting surface 52 is a substantially flat, planar surface that is selectively engaged by the cutting blade 54, i.e. during a cutting operation. Alternatively, the cutting surface 52 can be other than a substantially flat, planar surface. For example, the cutting surface 52 can have a somewhat convex or concave curvature. Additionally, in certain embodiments, the cutting blade 54 can be fixedly or removably secured to the second arm 14 and/or integrally formed with the second arm 14. The design and features of certain embodiments of the cutting blade 54 will be described in greater detail herein below.

When it is desired to cut a hair (not illustrated), e.g., an eyelash and/or an eyebrow hair, that may be positioned in a somewhat delicate and/or hard-to-access area, the user of the cutting device 10 can apply pressure on the outer surfaces 16, 34 of the first arm 12 and the second arm 14, respectively, such that the arms 12, 14 move toward one another. More particularly, sufficient movement of the arms 12, 14 toward one another causes the cutting blade 54 to selectively contact and/or engage the cutting surface 52 thereby enabling the cutting blade 46 to cut a hair that is positioned between the cutting blade 54 and the cutting surface 52.

In some embodiments, the shape of the second arm outer surface 34 can vary along the length of the second arm 14. More specifically, in one such embodiment, the second arm outer surface 34 can be a substantially flat, planar surface through the second arm connected section 42 and at least a majority of the second arm diverging section 44; and the second arm outer surface 34 can be curved or rounded near the second arm distal end 40, e.g., through the second arm converging section 46 and possibly a small portion of the second arm diverging section 44. Additionally, the first arm outer surface 16 can also vary in a similar manner along the length of the first arm 12. With this design, the cutting device 10 can be easy to grip for the user, i.e. along the substantially flat, planar surfaces of the outer surfaces 16, 34, and the cutting device 10 can exhibit stronger cutting capabilities, i.e. with the somewhat rounded surfaces of the outer surfaces 16, 34, within the converging sections 28, 46 and where the cutting blade 54 selectively engages the cutting surface 52. Alternatively, the shape of the outer surfaces 16, 34 can be substantially consistent along the full length of the arms 12, 14, respectively, and/or the shape of the outer surfaces 16, 34 can vary in a different manner along the length of the arms 12, 14.

Figure 2A:
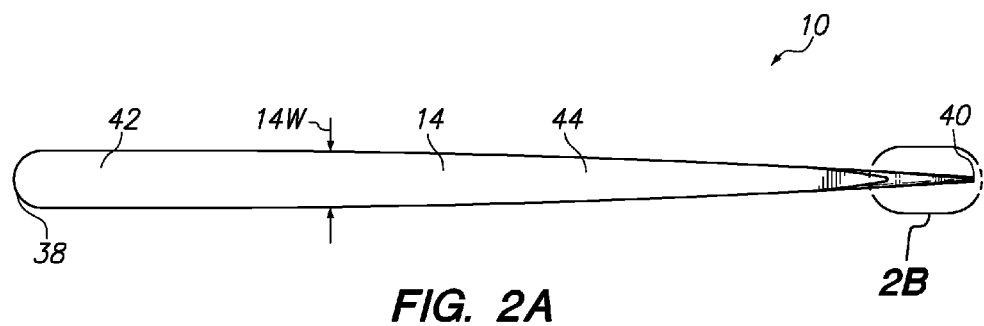
FIG. 2A is a side view of the hair cutting device illustrated in FIG. 1.

FIG. 2A is a side view of the hair cutting device 10 illustrated in FIG. 1. More particularly, FIG. 2A is a view looking directly at the second arm 14 of the hair cutting device 10. Additionally, FIG. 2B is a close-up view of a portion of the hair cutting device 10 illustrated in the dashed oval in FIG. 2A.

As shown in FIG. 2A, and as noted above, the second arm width 14W of the second arm 14 tapers generally inwardly, i.e. narrows, from the second arm proximal end 38 to the second arm distal end 40. Additionally, as illustrated in FIG. 2B, the first arm width 12W of the first arm 12 also tapers generally inwardly, i.e. narrows, toward to first arm distal end 22. Moreover, in this embodiment, the first arm width 12W and the second arm width 14W are substantially identical through a majority of the length of the cutting device 10. Stated in another manner, the first arm width 12W and the second arm width 14W can be substantially identical through the connected sections 24 (illustrated in FIG. 1), 42 and/or at least a majority of the diverging sections 26 (illustrated in FIG. 1), 44 of the first arm 12 and the second arm 14, respectively.

Figure 2B:
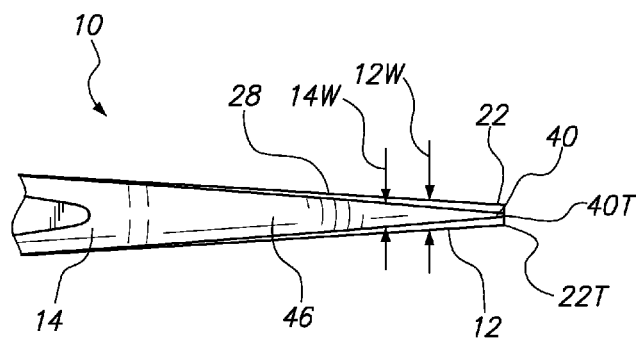
FIG. 2B is a close-up view of a portion of the hair cutting device illustrated in the dashed oval in FIG. 2A.

In certain embodiments, as shown in FIG. 2B, the first arm distal end 22 and the second arm distal end 40 can be positioned somewhat adjacent to one another, i.e. the arms 12, 14 can be substantially equal in length, but the distal ends 22, 40 can be designed differently from one another. For example, as illustrated in FIG. 2B, the first arm distal end 22 includes a substantially flat, blunted first arm tip 22T, and the second arm distal end 40 includes a sharp, pointed second arm tip 40T. With this design, near the distal ends 22, 40 of each of the arms 12, 14, e.g., in the converging sections 28, 46 of each of the arms 12, 14, the second arm 14 is slightly narrower than the first arm 12. Stated in another manner, the second arm width 14W at the second arm distal end 40 is smaller than the first arm width 12W at the first arm distal end 22. Alternatively, the first arm distal end 22 and the second arm distal end 40 can be designed in a similar manner to one another, and/or the distal ends 22, 40 can have different designs than those specifically illustrated in the Figures.

Figure 3:
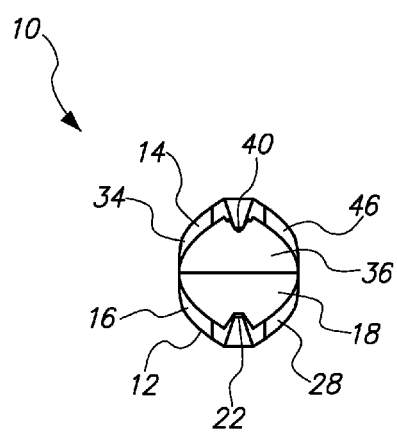
FIG. 3 is an end view of the hair cutting device illustrated in FIG. 1, taken from the right side of the device as illustrated in FIG. 2A.

FIG. 3 is an end view of the hair cutting device 10 illustrated in FIG. 1, taken from the right side of the device 10 as illustrated in FIG. 2A. More specifically, FIG. 3 is an end view of the cutting device 10 looking in at the distal ends 22, 40 of each of the first arm 12 and the second arm 14. FIG. 3 illustrates certain features and aspects of the design of the inner surfaces 18, 36 of the first arm 12 and the second arm 14, respectively, as well as certain features and aspects of the design of the outer surfaces 16, 34 of the arms 12, 14 near the distal ends 22, 40 of the arms 12, 14, i.e. in the converging sections 28, 46 of the arms 12, 14.

Figure 4:
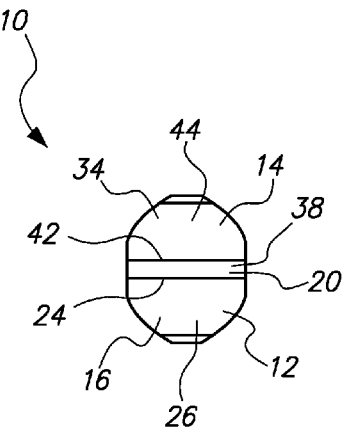
FIG. 4 is an opposing end view of the hair cutting device illustrated in FIG. 1, taken from the left side of the device as illustrated in FIG. 2A.

FIG. 4 is an opposing end view of the hair cutting device 10 illustrated in FIG. 1, taken from the left side of the device 10 as illustrated in FIG. 2A. More specifically, FIG. 4 is an end view of the cutting device 10 looking in at the proximal ends 20, 38 of each of the first arm 12 and the second arm 14. FIG. 4 illustrates certain features and aspects of the design of the outer surfaces 16, 34 of the first arm 12 and the second arm 14 through the connected sections 24, 42 and the diverging sections 26, 44 of the arms 12, 14.

Figure 5:
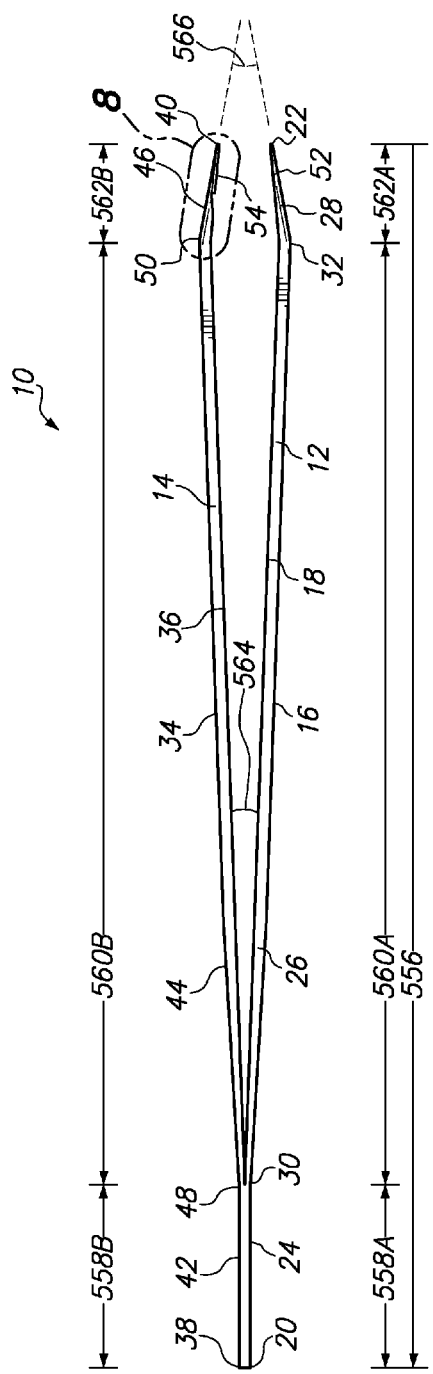
FIG. 5 is a top view of the hair cutting device illustrated in FIG. 1, shown in an open position.
Figure 6:
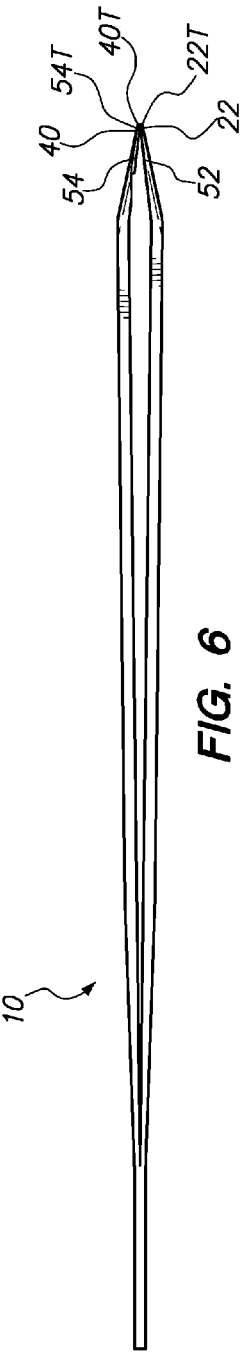
FIG. 6 is a top view of the hair cutting device illustrated in FIG. 1, shown in a partially closed position.
Figure 7:
FIG. 7 is a top view of the hair cutting device illustrated in FIG. 1, shown in a substantially closed position.

FIGS. 5-7 illustrate the general movement of the cutting device 10 through a cutting operation, i.e. from an open (relaxed) position where the cutting blade 54 does not contact and/or engage the cutting surface 52 to a closed (or at least a substantially closed) position where the cutting blade 54 at least substantially fully engages the cutting surface 52 along the full length of the cutting blade 54. More particularly, FIG. 5 is a top view of the hair cutting device 10 illustrated in FIG. 1, shown in the open position; FIG. 6 is a top view of the hair cutting device 10 illustrated in FIG. 1, shown in a partially closed position; and FIG. 7 is a top view of the hair cutting device 10 illustrated in FIG. 1, shown in a substantially closed position.

As illustrated, and as described in detail above, FIG. 5 shows that the first arm 12 of the cutting device 10 can include the first arm outer surface 16, the first arm inner surface 18, the first arm proximal end 20 and the first arm distal end 22.

Additionally, FIG. 5 further illustrates that the first arm 12 includes the first arm connected section 24, the first arm diverging section 26, and the first arm converging section 28. The lengths of the first arm connected section 24, the first arm diverging section 26 and the first arm converging section 28 can be varied relative to an overall device length 556 of the cutting device 10. For example, in certain embodiments, the first arm connected section 24 can have a connected length 558A of between a range of greater than approximately five percent and less than approximately twenty-five percent of the overall device length 556; the first arm diverging section 26 can have a diverging length 560A of between a range of greater than approximately sixty percent and less than approximately eighty-five percent of the overall device length 556; and the first arm converging section 28 can have a converging length 562A of between a range of greater than approximately two percent and less than approximately twenty percent of the overall device length 556. Alternatively, in certain embodiments, the first arm connected section 24 can have a connected length 558A of between a range of greater than approximately ten percent and less than approximately twenty percent of the overall device length 556; the first arm diverging section 26 can have a diverging length 560A of between a range of greater than approximately seventy percent and less than approximately eighty percent of the overall device length 556; and the first arm converging section 28 can have a converging length 562A of between a range of greater than approximately five percent and less than approximately fifteen percent of the overall device length 556. Still alternatively, the connected length 558A, the diverging length 560A and the converging length 562A of the first arm 12 can have different ranges and/or values than those specifically discussed above.

Similarly, as illustrated, and as described in detail above, FIG. 5 shows that the second arm 14 of the cutting device 10 can include the second arm outer surface 34, the second arm inner surface 36, the second arm proximal end 38 and the second arm distal end 40.

Additionally, FIG. 5 further illustrates that the second arm 14 includes the second arm connected section 42, the second arm diverging section 44, and the second arm converging section 46. The lengths of the second arm connected section 42, the second arm diverging section 44 and the second arm converging section 46 can be varied relative to the overall device length 556 of the cutting device 10. For example, in certain embodiments, the second arm connected section 42 can have a connected length 558B of between a range of greater than approximately five percent and less than approximately twenty-five percent of the overall device length 556; the second arm diverging section 44 can have a diverging length 560B of between a range of greater than approximately sixty percent and less than approximately eighty-five percent of the overall device length 556; and the second arm converging section 46 can have a converging length 562B of between a range of greater than approximately two percent and less than approximately twenty percent of the overall device length 556. Alternatively, in certain embodiments, the second arm connected section 42 can have a connected length 558B of between a range of greater than approximately ten percent and less than approximately twenty percent of the overall device length 556; the second arm diverging section 44 can have a diverging length 560B of between a range of greater than approximately seventy percent and less than approximately eighty percent of the overall device length 556; and the second arm converging section 46 can have a converging length 562B of between a range of greater than approximately five percent and less than approximately fifteen percent of the overall device length 556. Still alternatively, the connected length 558B, the diverging length 560B and the converging length 562B of the second arm 14 can have a range or value that is different than the ranges or values specifically discussed above.

In certain embodiments, the connected length 558A, the diverging length 560A and the converging length 562A of the first arm 12 can be substantially similar, if not identical to, the connected length 558B, the diverging length 560B and the converging length 562B of the second arm 14, respectively. Alternatively, the connected length 558A, the diverging length 560A and/or the converging length 562A of the first arm 12 can be different than the connected length 558B, the diverging length 560B and the converging length 562B of the second arm 14, respectively.

Further, FIG. 5 also illustrates a diverging angle 564 that can exist between the first arm diverging section 26 and the second arm diverging section 44 when the cutting device 10 is in the open (relaxed) position. In certain embodiments, the diverging angle 564 can be between a range of greater than approximately two degrees and less than approximately fifteen degrees. Alternatively, the diverging angle 564 can be greater than approximately fifteen degrees or less than approximately two degrees.

Still further, FIG. 5 illustrates a converging angle 566 that can exist between the first arm converging section 28 and the second arm converging section 46 when the cutting device 10 is in the open (relaxed) position. In certain embodiments, the converging angle 566 can be between a range of greater than approximately ten degrees and less than approximately twenty-five degrees. Alternatively, the converging angle 566 can be greater than approximately twenty-five degrees or less than approximately ten degrees.

As noted, FIG. 5 illustrates the cutting device 10 in the open (relaxed) position, i.e. before the user has placed any pressure on the outer surfaces 16, 34 of the first arm 12 and/or the second arm 14, respectively, for purposes of initiating a cutting operation.

Additionally, as noted, FIG. 6 illustrates the cutting device 10 in a partially closed position. More specifically, FIG. 6 illustrates the cutting device 10 at a time when a blade tip 54T of the cutting blade 54, i.e. a portion of the cutting blade 54 at a distal end of the cutting blade 54 that is nearest to the second arm tip 40T of the second arm distal end 40, first contacts and/or engages the cutting surface 52. In one embodiment, as shown, the blade tip 54T can substantially coincide with second arm tip 40T, i.e. the cutting blade 54 can extend fully to and/or from the second arm tip 40T of the second arm distal end 40. In such embodiment, the initial contact between the cutting blade 54 and the cutting surface 52 occurs when the blade tip 54T first contacts and/or engages the first arm tip 22T, i.e. when the blade tip 54T first contacts and/or engages the cutting surface 52 that is formed near, at and/or substantially adjacent to the first arm tip 22T of the first arm distal end 22.

Further, as noted, FIG. 7 illustrates the cutting device 10 in a substantially closed position. More specifically, FIG. 7 illustrates the cutting device 10 at a time when the cutting blade 54 is substantially fully engaged with the cutting surface 52.

It should be appreciated that with the specific design and orientation of the cutting blade 54 relative to the cutting surface 52, as illustrated herein, the cutting blade 54 provides a gradual, progressive cutting motion from the time that the blade tip 54T initially contacts the cutting surface 52 (i.e. at the first arm tip 22T) until the time that the cutting blade 54 is substantially fully engaged with the cutting surface 52. Stated in another manner, in this embodiment, the cutting blade 54 gradually and progressively engages the cutting surface 52 along the full length of the cutting blade 54 from the initial contact of the blade tip 54T (i.e. the distal end (outer edge) of the cutting blade 54) to a proximal end (inner edge) of the cutting blade 54. With this design, the cutting device is able to quickly and effectively cut any hair (not illustrated) that may be positioned between the cutting blade 54 and the cutting surface 52.

Figure 8:
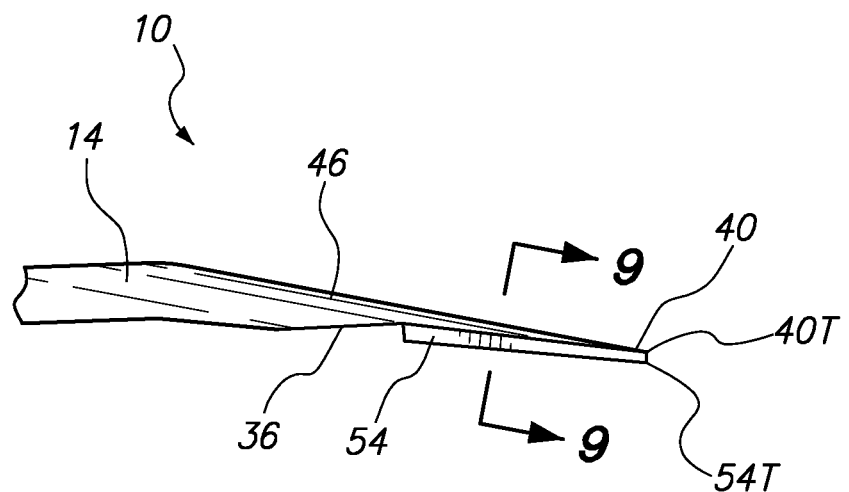
FIG. 8 is a close-up view of a portion of the hair cutting device illustrated in the dashed oval in FIG. 5, including a cutting blade.

FIG. 8 is a close-up view of a portion of the hair cutting device 10 illustrated in the dashed oval in FIG. 5. In particular, FIG. 8 primarily illustrates the second arm converging section 46 and the cutting blade 54 that is positioned along the second arm inner surface 36 near the second arm distal end 40.

As illustrated, in this embodiment, the blade tip 54T of the cutting blade 54 substantially coincides with the second arm tip 40T of the second arm 14. Stated in another manner, the cutting blade 54 extends substantially fully to and/or from the second arm distal end 40. With this design, there is no concern of any other portion of the second arm 14 near the second arm distal end 40 contacting any portion of the first arm 12 (illustrated, for example, in FIG. 1) prior to the cutting blade 54 contacting and/or engaging the cutting surface 52 (illustrated, for example, in FIG. 1).

Figure 9:
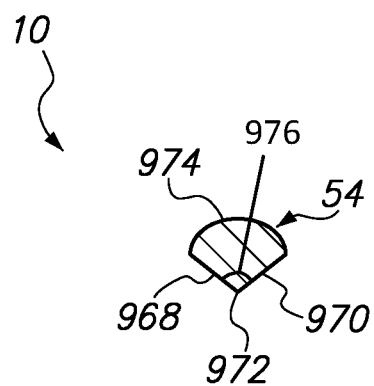
FIG. 9 is a cross-sectional view of a portion of the hair cutting device including the cutting blade, taken on line 9-9 in FIG. 8.

FIG. 9 is a cross-sectional view of a portion of the hair cutting device 10 taken on line 9-9 in FIG. 8. More specifically, FIG. 9 provides a cross-sectional view of the cutting blade 54.

The design of the cutting blade 54 can be varied. As illustrated, in one embodiment, the cutting blade 54 has a somewhat wedge-shaped cross-section, and includes a first angled side 968 and a second angled side 970 that converge toward one another to provide a sharp, cutting edge 972; and a curved outer surface 974, e.g., a convex curved outer surface, that is directly on the opposite side of the cutting blade from the cutting edge 972. As shown in the embodiment in FIG. 9, the cutting edge 972 can have a blade angle 976 that is greater than seventy-five degrees. In a non-exclusive alternative embodiment, the cutting edge 972 can have a blade angle of 976 of greater than 100 degrees. Still alternatively, the cutting edge 972 can have a blade angle 976 of at least 110 degrees. Additionally, as clearly illustrated in FIG. 9, the convex curved outer surface 974 is curved in a direction that is transverse, or perpendicular, to the length of the cutting edge 972. With this design, the cutting blade 54 can exhibit greater strength characteristics and is able to provide a stronger, more reliable cutting motion. Alternatively, the cutting blade 54 can have a different shape and/or design. For example, in one non-exclusive alternative embodiment, the cutting blade 54 can have a substantially flat outer surface.

As described herein, it should be appreciated that the cutting edge 972 of the cutting blade 54 is the specific portion of the cutting blade 54 that contacts and/or engages the cutting surface 52 during a cutting operation.

It is understood that although a number of different embodiments of the hair cutting device 10 have been illustrated and described herein, one or more features of any one embodiment can be combined with one or more features of one or more of the other embodiments, provided that such combination satisfies the intent of the present invention.

While a number of exemplary aspects and embodiments of the hair cutting device 10 have been discussed above, those skilled in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A hair cutting device comprising:
   a first arm having (i) a first arm proximal end, (ii) a first arm distal end, (iii) a first arm connected section that extends away from the first arm proximal end, (iv) a first arm diverging section that extends away from the first arm connected section, (v) a first arm converging section that extends away from the first arm diverging section to the first arm distal end, (vi) a cutting surface formed along a first arm inner surface of the first arm adjacent to the first arm distal end, and a first arm angle adjustment point that defines a junction between the first arm diverging section and the first arm converging section; and
   an opposed second arm having (i) a second arm proximal end, (ii) a second arm distal end, (iii) a second arm connected section that extends away from the second arm proximal end, the second arm connected section being secured to the first arm connected section, (iv) a second arm diverging section that extends away from the second arm connected section, the second arm diverging section gradually diverging away from the first arm diverging section, (v) a second arm converging section that extends away from the second arm diverging section to the second arm distal end, the second arm converging section gradually converging toward the first arm converging section, (vi) a second arm angle adjustment point that defines a junction between the second arm diverging section and the second arm converging section, the first arm and the second arm being symmetrical relative to one another from the proximal ends to the angle adjustment points, and (vii) a cutting blade along a second arm inner surface of the second arm adjacent to the second arm distal end, the cutting blade being integrally formed with the second arm, the cutting blade being configured to selectively engage the cutting surface during a cutting operation, the cutting blade including a first angled side and a second angled side that converge toward one another to provide a sharp, cutting edge, the cutting edge having a blade angle that is greater than ninety degrees, the blade angle being measured in a direction that is transverse to a length of the cutting edge;

wherein the first arm flexes along the first arm converging section between the first arm angle adjustment point and the cutting surface when the cutting blade is selectively engaging the cutting surface during the cutting operation; and wherein the second arm flexes along the second arm converging section between the second arm angle adjustment point and the cutting blade when the cutting blade is selectively engaging the cutting surface during the cutting operation.

2. The hair cutting device of claim 1 wherein the cutting edge is configured to gradually engage the cutting surface during the cutting operation along a full length of the cutting blade from an initial contact of a blade tip at a distal end of the cutting blade to a proximal end of the cutting blade, the blade tip being a portion of the cutting blade that is nearest to a second arm tip of the second arm distal end.

3. The hair cutting device 1 wherein the first arm includes a first arm width and the second arm includes a second arm width, and wherein the second arm width adjacent to the second arm distal end is narrower than the first arm width adjacent to the first arm distal end.

4. The hair cutting device of claim 1 wherein the first arm distal end includes a flat, blunted first arm tip, and wherein the second arm distal end includes a sharp, pointed second arm tip.

5. The hair cutting device of claim 1 wherein the first arm connected section has a connected length of between a range of greater than ten percent and less than twenty percent of an overall device length; wherein the first arm diverging section has a diverging length of between a range of greater than seventy percent and less than eighty percent of the overall device length; and wherein the first arm converging section has a converging length of between a range of greater than five percent and less than fifteen percent of the overall device length.

6. The hair cutting device of claim 5 wherein the second arm connected section has a connected length that is equal to the connected length of the first arm connected section; wherein the second arm diverging section has a diverging length that is equal to the diverging length of the first arm diverging section; and wherein the second arm converging section has a converging length that is equal to the converging length of the first arm converging section.

7. The hair cutting device of claim 1 wherein the first arm diverging section and the second arm diverging section diverge from one another at a diverging angle of between a range of greater than two degrees and less than ten degrees when the cutting device is in an open position.

8. The hair cutting device of claim 1 wherein the first arm converging section and the second arm converging section converge toward one another at a converging angle of between a range of greater than ten degrees and less than twenty-five degrees when the cutting device is in an open position.

9. A hair cutting device comprising:
a first arm having (i) a first arm proximal end, (ii) a first arm distal end, (iii) a first arm connected section that extends away from the first arm proximal end, (iv) a first arm diverging section that extends away from the first arm connected section, (v) a first arm converging section that extends away from the first arm diverging section to the first arm distal end, (vi) a first arm angle adjustment point that defines a junction between the first arm diverging section and the first arm converging section, and (vii) a cutting surface formed along a first arm inner surface of the first arm adjacent to the first arm distal end; and
an opposed second arm having (i) a second arm proximal end, (ii) a second arm distal end, (iii) a second arm connected section that extends away from the second arm proximal end, the second arm connected section being secured to the first arm connected section, (iv) a second arm diverging section that extends away from the second arm connected section, the second arm diverging section gradually diverging away from the first arm diverging section, (v) a second arm converging section that extends away from the second arm diverging section to the second arm distal end, the second arm converging section gradually converging toward the first arm converging section, (vi) a second arm angle adjustment point that defines a junction between the second arm diverging section and the second arm converging section, and (vii) a cutting blade along a second arm inner surface of the second arm adjacent to the second arm distal end, the cutting blade being configured to selectively engage the cutting surface during a cutting operation, the cutting blade including a first angled side and a second angled side that converge toward one another to provide a sharp, cutting edge, the cutting edge having a blade angle that is greater than ninety degrees, the blade angle being measured in a direction that is transverse to a length of the cutting edge;
wherein the first arm and the second arm are symmetrical relative to one another from the proximal ends to the angle adjustment points;
wherein the first arm flexes along the first arm converging section between the first arm angle adjustment point and the cutting surface when the cutting blade is selectively engaging the cutting surface during the cutting operation; and
wherein the second arm flexes along the second arm converging section between the second arm angle adjustment point and the cutting blade when the cutting blade is selectively engaging the cutting surface during the cutting operation.

10. The hair cutting device of claim 9 wherein the cutting edge is configured to gradually engage the cutting surface during the cutting operation along a full length of the cutting blade from an initial contact of a blade tip at a distal end of the cutting blade to a proximal end of the cutting blade, the blade tip being a portion of the cutting blade that is nearest to a second arm tip of the second arm distal end.

11. The hair cutting device 32 wherein the first arm includes a first arm width and the second arm includes a second arm width, and wherein the second arm width adjacent to the second arm distal end is narrower than the first arm width adjacent to the first arm distal end.

12. The hair cutting device of claim 9 wherein the first arm distal end includes a flat, blunted first arm tip, and wherein the second arm distal end includes a sharp, pointed second arm tip.

13. The hair cutting device of claim 9 wherein the first arm connected section has a connected length of between a range of greater than ten percent and less than twenty percent of an overall device length; wherein the first arm diverging section has a diverging length of between a range of greater than seventy percent and less than eighty percent of the overall device length; and wherein the first arm converging section has a converging length of between a range of greater than five percent and less than fifteen percent of the overall device length.

14. The hair cutting device of claim 9 wherein the first arm diverging section and the second arm diverging section diverge from one another at a diverging angle of between a range of greater than two degrees and less than ten degrees when the cutting device is in an open position.

15. The hair cutting device of claim 9 wherein the first arm converging section and the second arm converging section converge toward one another at a converging angle of between a range of greater than ten degrees and less than twenty-five degrees when the cutting device is in an open position.

16. A hair cutting device comprising:
a first arm having (i) a first arm proximal end, (ii) a first arm distal end including a flat, blunted first arm tip, (iii) a first arm connected section that extends away from the first arm proximal end, (iv) a first arm diverging section that extends away from the first arm connected section, (v) a first arm converging section that extends away from the first arm diverging section to the first arm distal end, (vi) a first arm angle adjustment point that defines a junction between the first arm diverging section and the first arm converging section, (vii) a cutting surface formed along a first arm inner surface of the first arm adjacent to the first arm distal end, and (viii) a first arm width; and
an opposed second arm having (i) a second arm proximal end, (ii) a second arm distal end including a sharp, pointed second arm tip, (iii) a second arm connected section that extends away from the second arm proximal end, the second arm connected section being secured to the first arm connected section, (iv) a second arm diverging section that extends away from the second arm connected section, the second arm diverging section gradually diverging away from the first arm diverging section, (v) a second arm converging section that extends away from the second arm diverging section to the second arm distal end, the second arm converging section gradually converging toward the first arm converging section, (vi) a second arm angle adjustment point that defines a junction between the second arm diverging section and the second arm converging section, (vii) a cutting blade along a second arm inner surface of the second arm adjacent to the second arm distal end, the cutting blade being configured to selectively engage the cutting surface during a cutting operation, the cutting blade including a first angled side and a second angled side that converge toward one another to provide a sharp, cutting edge, the cutting edge having a blade angle that is greater than ninety degrees, the blade angle being measured in a direction that is transverse to a length of the cutting edge, and (viii) a second arm width, the second arm width of the second arm converging section being narrower than the first arm width of the first arm converging section;
wherein the first arm and the second arm are symmetrical relative to one another from the proximal ends to the angle adjustment points;
wherein the first arm flexes along the first arm converging section between the first arm angle adjustment point and the cutting surface when the cutting blade is selectively engaging the cutting surface during the cutting operation;
wherein the second arm flexes along the second arm converging section between the second arm angle adjustment point and the cutting blade when the cutting blade is selectively engaging the cutting surface during the cutting operation; and
wherein the cutting edge is configured to gradually engage the cutting surface during the cutting operation along a full length of the cutting blade from an initial contact of a blade tip at a distal end of the cutting blade to a proximal end of the cutting blade, the blade tip being a portion of the cutting blade that is nearest to the second arm tip of the second arm distal end.

* * * * *

UNITED STATES PATENT AND TRADEMARK OFFICE
CERTIFICATE OF CORRECTION

PATENT NO. : 10,123,605 B2
APPLICATION NO. : 14/566626
DATED : November 13, 2018
INVENTOR(S) : Linda Luu Page 1 of 1

It is certified that error appears in the above-identified patent and that said Letters Patent is hereby corrected as shown below:

In the Claims

Column 12, Line 66, replace "32" with --9--.

Signed and Sealed this
Nineteenth Day of February, 2019

Andrei Iancu
*Director of the United States Patent and Trademark Office*